United States Patent [19]

Chapelon et al.

[11] Patent Number: 5,738,635
[45] Date of Patent: Apr. 14, 1998

[54] ADJUSTABLE FOCUSING THERAPEUTIC APPARATUS WITH NO SECONDARY FOCUSING

[75] Inventors: Jean-Yves Chapelon, Villeurbanne; Dominique Cathignol, Genas; Emmanuel Blanc, St.-Genis-Laval, all of France

[73] Assignee: Technomed Medical Systems, Vaux En Velin, France

[21] Appl. No.: 629,922

[22] Filed: Apr. 10, 1996

Related U.S. Application Data

[63] Continuation of Ser. No. 307,719, filed as PCT/FR94/00070, Jan. 21, 1994, published as WO94/17514, published as Apr. 8, 1994, abandoned.

[30] Foreign Application Priority Data

Jan. 22, 1993 [FR] France .................. 93 00662

[51] Int. Cl.$^6$ .................................................. A61B 17/22
[52] U.S. Cl. .................................................. 601/2; 601/3
[58] Field of Search .................. 601/2–4; 128/660.03; 367/905, 100; 310/314, 316, 317, 318

[56] References Cited

U.S. PATENT DOCUMENTS

| | | | |
|---|---|---|---|
| 3,757,256 | 9/1973 | Whitehouse et al. | 333/151 |
| 3,958,559 | 5/1976 | Glenn et al. | 601/2 |
| 4,282,452 | 8/1981 | Hassler et al. | 310/317 |
| 4,875,487 | 10/1989 | Seppi . | |
| 5,065,629 | 11/1991 | Koike et al. | 367/100 |
| 5,209,221 | 5/1993 | Riedlinger | 601/2 |
| 5,261,408 | 11/1993 | Maslak et al. | 128/661.01 |

OTHER PUBLICATIONS

Ebbini et al., "Experimental Evaluation of a Prototype Cylindrical Section Ultrasound Hyperthermia Phased–Array Applicator", *IEEE Transactions on Ultrasonics, Ferroelectrics, and Frequency Control*, vol. 38, No. 5, Sep. 1991, New York, USA, pp. 510–520.

Umemura et al., "The Sector–Vortex Phased Array: Acoustic Field Synthesis for Hyperthermia", *IEEE Transactions on Ultrasonics, Ferroelectrics, and Frequency Control*, vol. 36, No. 2, Mar. 1989, New York, USA, pp. 249–257.

O'Donnell, "Coded Excitation System for Improving the Penetration of Real–Time Phased–Array Imaging System", *IEEE Transactions on Ultrasonics, Ferroelectrics and Frequency Control*, vol. 39, No. 3, May 1992, New York, USA, pp. 341–351.

*Primary Examiner*—Brian L. Casler
*Attorney, Agent, or Firm*—Welsh & Katz, Ltd.

[57] ABSTRACT

The invention relates to the use of Dirac-type autocorrelation function signals for powering multielements ultrasonic transducers used in therapeutic application in order to minimize or eliminate secondary focusing. The Dirac-type autocorrelation function signals may be generated by a pseudo random binary code.

16 Claims, 8 Drawing Sheets

ADJUSTABLE FOCUSING THERAPEUTIC APPARATUS WITH NO SECONDARY FOCUSING

This is a continuation of application Ser. No. 08/307,719, filed as PCT/FR94/00070, Jan. 21, 1994 published as WO94/17514, Apr. 8, 1994, now abandoned.

BACKGROUND OF THE INVENTION

This invention is chiefly related to apparatus for therapy having variable focusing and no secondary spurious focusing.

Preferably, the apparatus uses focalized ultrasounds. The invention also entails the use of an electronic signal which has an autocorrelation function of Dirac type for the excitation of at least one ultrasonic transducer element. The invention also relates to a process of electronic focusing by at least one transducer element which eliminates or minimizes secondary focusing by exciting the transducer elements with an electronic signal generator which produces an electronic signal having a Dirac type autocorrelation function.

It is well-known that piezo-electric transducers produce therapeutic focalized ultrasounds or an ultrasonic beam when powered by electronic signals of sine type. The ultrasonic beam can create lesions in tissue where such lesions are limited to the focal volume of the transducer. This spatial limitation, is notably necessary for an efficient treatment in the area of cancers therapy such as cancer of the prostate, of the breast, of the brain etc. The beams can also be used in the treatment of benign lesions such as benign prostatic hypertrophy, benign breast lesions, and nodules of the thyroid.

Generally, these cancers have a predetermined volume so that it is necessary to scan the focal point of the transducer in order to treat the entire lesion.

This motion can be obtained by mechanical means, i.e. translation stages which are expensive and bulky. However it is also possible to use electronic means for the scanning for the focal point. These means are less cumbersome, less expensive, and eliminate the need of mechanical motions of the transducer. These mechanical motions can degrade the physical contact between the transducer and the patient and are detrimental to the proper transmission of the acoustic waves. In addition these mechanical motion can cause unwanted motions of the target area during the treatment.

When using electronically focused transducers, the practitioner may lock the transducer head into position against the patient's skin, control the ultrasonic waves such that the deepest region of the target is treated, then change the control of the transducer to focus at a shorter distance to treat the most shallow region of the target. This procedure may result in less burns of the skin because these originate from using low aperture transducers. The aperture being the ratio between the diameter of the transducer and the focal distance, it is clear that the aperture is maximum when the treatment is delivered near the patient skin, hence the risk of burns is minimized.

These electronic steering means of the focal point must involve multi-element transducers. These elements can be shaped as concentric rings so that the focal point can be steered along the axis of the transducer, i.e. in the direction of the propagation of the waves. Multi-element two dimensional arrays of transducers elements must be used to steer the focal point in the three dimensions.

A physical motion of the focal point is obtained when sine waves are applied to these elements, these sine waves having a predetermined phase shift with respect to one another.

It is well-known to the one skilled in the art that for large displacement of the focal point an ambiguity may occur on the phase values which are applied to the signals of each of the elements of the transducer implying that secondary spurious focusing point appears within the ultrasonic field which may induce necrosis of the tissue in an unwanted area outside of the target thus rendering the apparatus dangerous and unfit for clinical To solve these problems several solutions have been proposed to control the ultrasonic field and obtain the desired ultrasonic field without secondary focusing points.

One example of known-methods includes the method of beam synthesis which was described by ES EBBINI in the article "Experimental evaluation of a prototype cylindrical section ultrasound hyperthermia phased array applicator" (in IEEE transactions on ultrasonics, ferroelectrics, and frequency control, Vol. 38, n°5, pp 510–520, Sept. 1991). In this method one calculates the amplitude and the phase of the signal to be applied to each element of the transducer in order to synthesize a predetermined beam geometry. One example is given on FIGS. 6,9,10, and 11 of the article. EBBINI shows that with this method it is possible to synthesize an ultrasonic field with one or several focusing points.

EBBINI's method has major drawback. Each transducer does not receive the maximum signal amplitude (see page 514). Thus, that the acoustic energy is not maximized. This is undesirable when treating a tissue with an endocavitary applicator which must be small so that the ratio between emitted power and transducer dimension must be maximum. However this constraint is acceptable for a low power hyperthermia treatment as foreseen in the article (see page 514).

An another method for synthesizing ultrasonic beams while limiting the number of spurious focal, points is described by UMEMURA in the article "The sector —vortex phased array: acoustic field synthesis for hyperthermia" also in IEEE transactions on ultrasonic, ferroelectrics and frequency control, Vol. 36, n°2, pp 249–257, Mar. 1989. This method is applicable to transducers divided in several sectors and consists in applying a specific phase distribution on each sector. Since it is necessary to subdivide the rings into sectors, this method's results in using a large number of transducers elements. To obtain a correct beam shape the number of elements must be high. Since the electronic circuits for the control of each element is complex, the cost of such an apparatus is very high and hardly compatible, with industrial and medical application where the cost of the therapy must be kept low.

The goal of the present invention is to solve the technical problem of electronic focusing of a therapeutic transducer ;over large scanning distances while eliminating spurious focal points and while using transducers to the maximum power and while keeping a spot-like focal area and at low cost such that the apparatus can be widely used.

The present invention offers for the first time a satisfactory solution to the technical problem as defined above and carries other technical advantages which will clearly appear to the one skilled in the art from the detailed description which follows.

SUMMARY OF THE INVENTION

According to a first aspect, the present invention introduces a process for the electronic focusing of at least one transducer element for therapy which eliminates or minimizes secondary focusing. According to the invention the transducer elements are excited by an electronic signal generator delivering an electronic signal of which the autocorrelation function is of DIRAC type.

The definition of the autocorrelation function is as follows.

Given temporal signal X(t) it carries the energy:

$$E_x = \int (X(t))^2 \, dt$$

the intercorrelation function between 2 signals X(t) and Y(t) is defined by $$\Gamma_{xy}(\tau) = \int X(t) \, Y(t-\tau) \, dt$$

This equation translates the similarity of the two signals X(t) and Y(t) when they are shifted in time by the delay τ. If this function is always null, the two signals are not correlated.

In the same way, the autocorrelation function of a signal is defined as:

$$\Gamma_{xx}(\tau) = \int X(t) \, X(t-\tau) \, dt$$

This function $\Gamma_{xx}(\tau)$ represents the similarity of function X taken at time t with itself but taken at time t−τ1. The less the similarity the more this function is closed to 0but its maximum is always at τ=0. In fact for any signal X(t) the autocorrelation ismmaximum for τ=0 since $\Gamma_{xx}(0)$ is nothing else but the energy $E_x$ of the signal.

One type of signal which is of interest corresponds to the wide-band signals. A signal is wide-band when the width of its autocorrelation function is narrow i.e. the autocorrelation function tends to a Dirac impulse δ(t). In the following we will call such a signal "signal with Dirac-type autocorrelation function".

Known examples of Dirac-type autocorrelation function are random signals of Gaussian or Poisonian-type signals which are modulated in frequency or phase Other examples of Dirac-type autocorrelation function include:

signals with "M" type sequence which are also known as "maximum length binary sequences" of the type described by Jean-Yves CHAPELON in chapter 6 page 225–236, and more especially page 230 in the book "Progress in medical imaging" edited by Dr Newhouse, Springer Verlag. N.Y., 1988.

"Golay" codes

"Barker" codes.

Coded pseudo random signals may be used directly or may modulate in phase or in frequency an electronic signal whose carrier-frequency matches the nominal frequency of the transducer.

It is better to use type "M" pseudo random coded signals. These are described precisely in "Progress in medical imaging". Briefly, these consist of sequences of binary signals which are assembled by the pseudo random repetition of impulses of an elementary duration. Each of these sequences is repeated with a repetition period T which is specific of a type "M" sequence.

A more precise description of type "M" sequence signal is described in FIG. 8:

the duration of the elementary pulse θ: 0.1μs <θ<100 μs. For example, the duration may be ideally of about 2 to 10 times the oscillating period of the transducer. Preferred value is about 1 μs.

repetition period T: 1 μs<T<10 s.

This pseudo random coded signals particularly of the type "M" which is preferred for the application are easily synthesized with electronic circuitry well-known by the one skilled in the art.

Using these Dirac-type autocorrelation function type electronic signals, it is possible, to eliminate all ambiguity in the definition of the time delays which results in a single focus of ultrasonic waves hence eliminating in a reliable way secondary focal zones which were present in the earlier devices.

According to a second aspect, the present invention also provides a therapeutic apparatus with electronic focusing which includes at least an ultrasonic transducer, a signal generator delivering an electronic signal, and a control device such that the signal generator delivers a Dirac-type autocorrelation function electronic signal.

The preferred embodiment of the signal or of the apparatus results from the description of the process above and of the claims.

In one or the other of the aspects above, according to a preferred embodiment mode, the signal generator delivers a Dirac-type autocorrelation function binary signal of the sequence "M" type and particularly having a maximal length.

Other characteristics will also appear to the one skilled in the art from the description below as well as from the claims which are also part of the description of the invention.

BRIEF DESCRIPTION OF THE DRAWINGS

The invention will now be described according to a preferred embodiment which is which is given only as an example and does not limit in any way the scope of the invention. In the drawings.

DETAILED DESCRIPTION OF THE DRAWINGS

Figure 1:
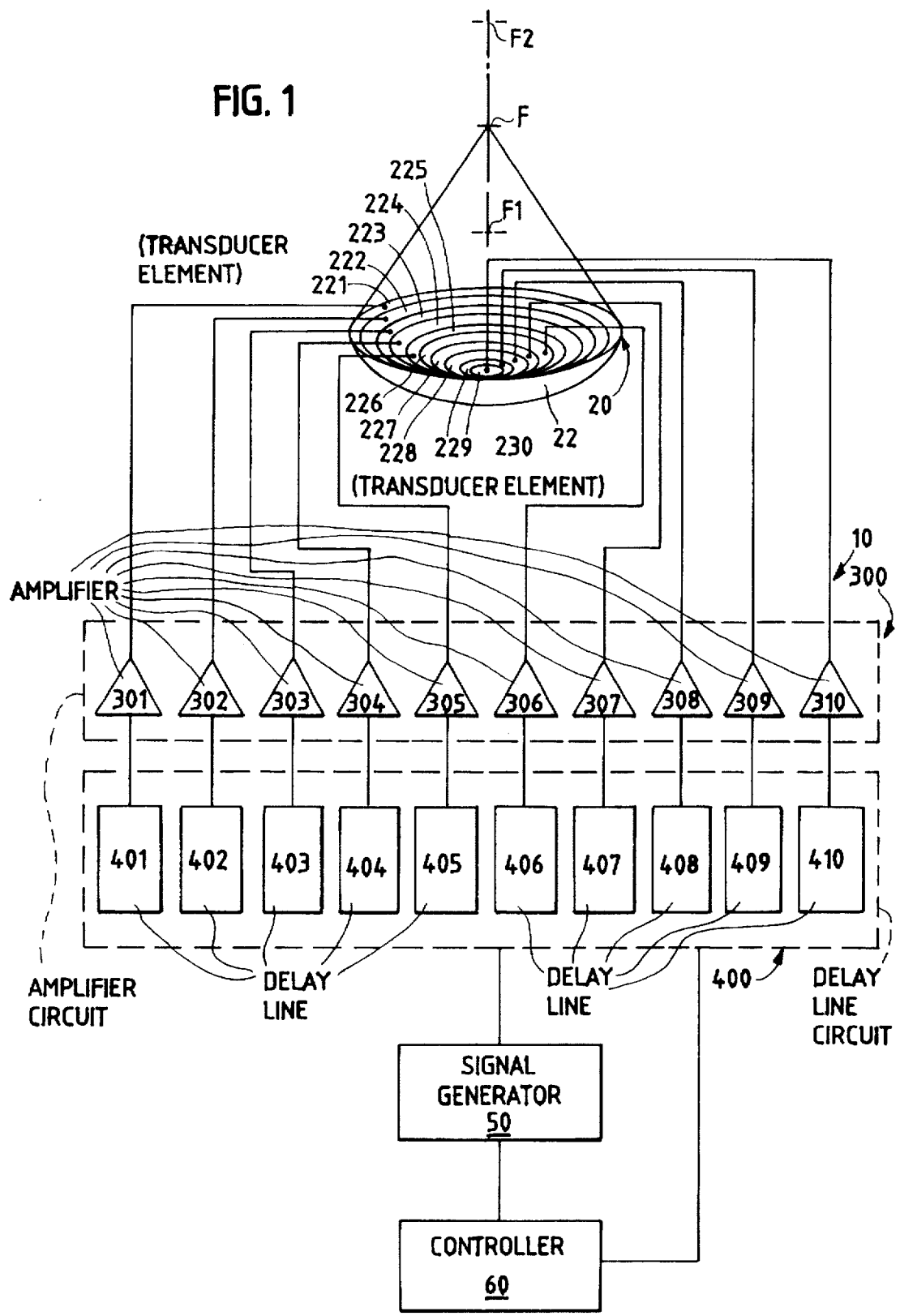
FIG. 1 represents the general schematics of therapeutic apparatus for treating living tissues, including a transducer array, the elementary transducers being shaped as rings so as to produce an electronic focusing along the axis of the transducer.

A therapeutic apparatus for treating living body tissues according to the prior art is represented by general reference number 10 in FIG. 1. This apparatus 10 includes a firing-head 20 which here is shaped as a naturally focalizing spherical cup 22 itself subdivided in an annular array of ring shaped piezoelectric transducer elements such as 221 to 230. Alternatively the cup could be subdivided as two-dimensional array (not represented here). This annular array or alternatively two-dimensional array is well-known to the one skilled in the art so that no further description is necessary. One example of an embodiment takes the form of spherical cup 22 of diameter 100 mm and of radius, i.e. focal length, 100 mm. Its frequency is about 1 MHz, its annular structure is made of 10 rings which have the same surface area and are separated one from the other by 0.1 mm spacing. Each transducer element 221–230 is connected to an amplifier 300 which includes elementary amplifiers 301–310 and a time delay device 400 which comprises elementary time delays 401–410 themselves connected to a signal generator 50 which is controlled by controller 60. In the figure, the generator 50 and the controller 60 are common to all elementary amplifiers and delay lines. Controller 60 also supplies the time delay to delay lines 401–410 calculated such that the electronic focusing occurs to the predetermined position on the axis.

With this design the device can generate an electronic focusing at any point on the axis of the transducer, between two boundary points F1 and F2.

In case the transducer is made of two dimensional array of elementary transducers a focal point can be obtained outside the main axis of the transducer.

The operation of this apparatus will now be described in reference to the curves in FIGS. 2–7 : respectively according to prior art (FIGS. 2–4) and according to the invention (FIG. 5–8).

Figure 2:
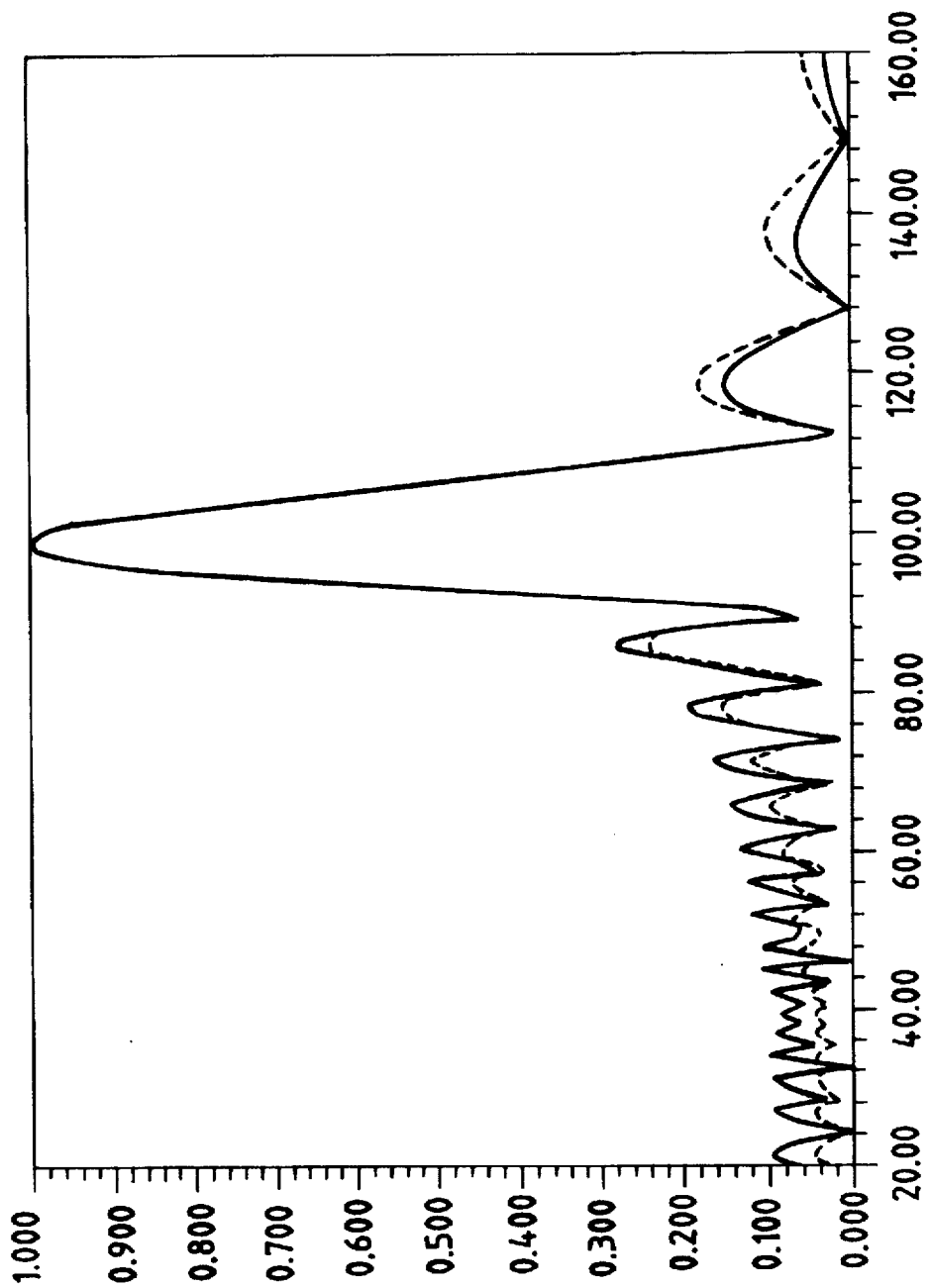
FIG. 2 represents an ultrasonic pressure curve (normalized to 1) versus the distance along the axis of the transducer (in millimeters). The transducer is the one in FIG. 1 with a diameter of 100 mm and geometric focus at 100 mm from the emitting surface. The curve in dashed lines is obtained in a non-absorbing coupling medium such as water. The curve in black is obtained in a medium similar to living body tissues, i.e. having an acoustical absorption of 0.1 Neper/cm. The transducers are excited with non de-phasing electronic sine signals according to prior art.

When generator 50 produces a typical sine wave electronic signal of frequency about 1 MHz and when no delay has been programmed into delay lines 401–410, one obtains natural focusing at the center of the spherical cup which is here 100 mm from the surface. Curve in FIG. 2 is, then obtained.

When controller 60 programs the following delays into delay lines 401–410, and the same signal generator 50 is used, one can move the focal point to 50 mm or to 130 mm (other delays would also move the focal point along the axis):

| RING No | FOCAL POINT 50 mm delays in μs | FOCAL POINT 130 mm delays in μs |
| --- | --- | --- |
| 1 | 0 | 0 |
| 2 | 1.2 | −0.3 |
| 3 | 2.4 | −0.6 |
| 4 | 3.5 | −0.9 |
| 5 | 4.6 | −1.2 |
| 6 | 5.7 | −1.5 |
| 7 | 6.7 | −1.8 |
| 8 | 7.8 | −2 |
| 9 | 8.8 | −2.3 |
| 10 | 9.8 | −2.7 |

Figure 3:
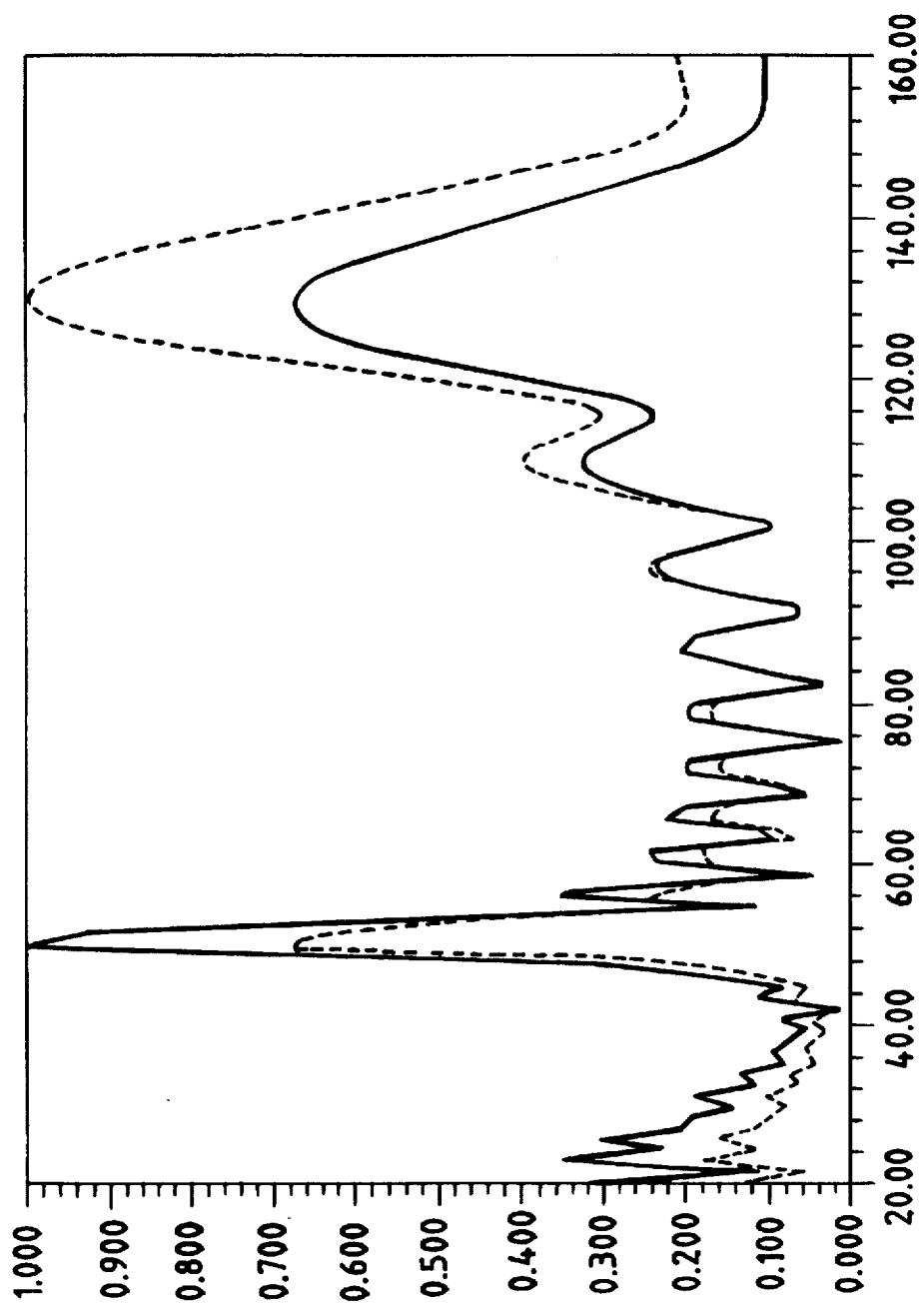
FIG. 3 is a curve similar to FIG. 2, obtained with the same transducer as FIG. 1 but the ring-elements are powered by sine type electronic signals which are phased such as to produce focal point 50 mm away from the emitting surface.

When the delays above are used to obtain an electronic focusing at 50 mm the curves on FIG. 3 are obtained. On these curves it is observed that a secondary focusing appears between 120 and 130 mm. However focusing is much attenuated by the absorption of the ultrasonic waves in the tissues (black curve) so that its influence on the therapeutic treatment may be negligible. If one does not take into account the absorption of the tissues the secondary focusing has an amplitude higher than the main focusing at 50 mm which demonstrates that there is a risk of occurrence of a secondary focusing which may impair safety.

Figure 4:
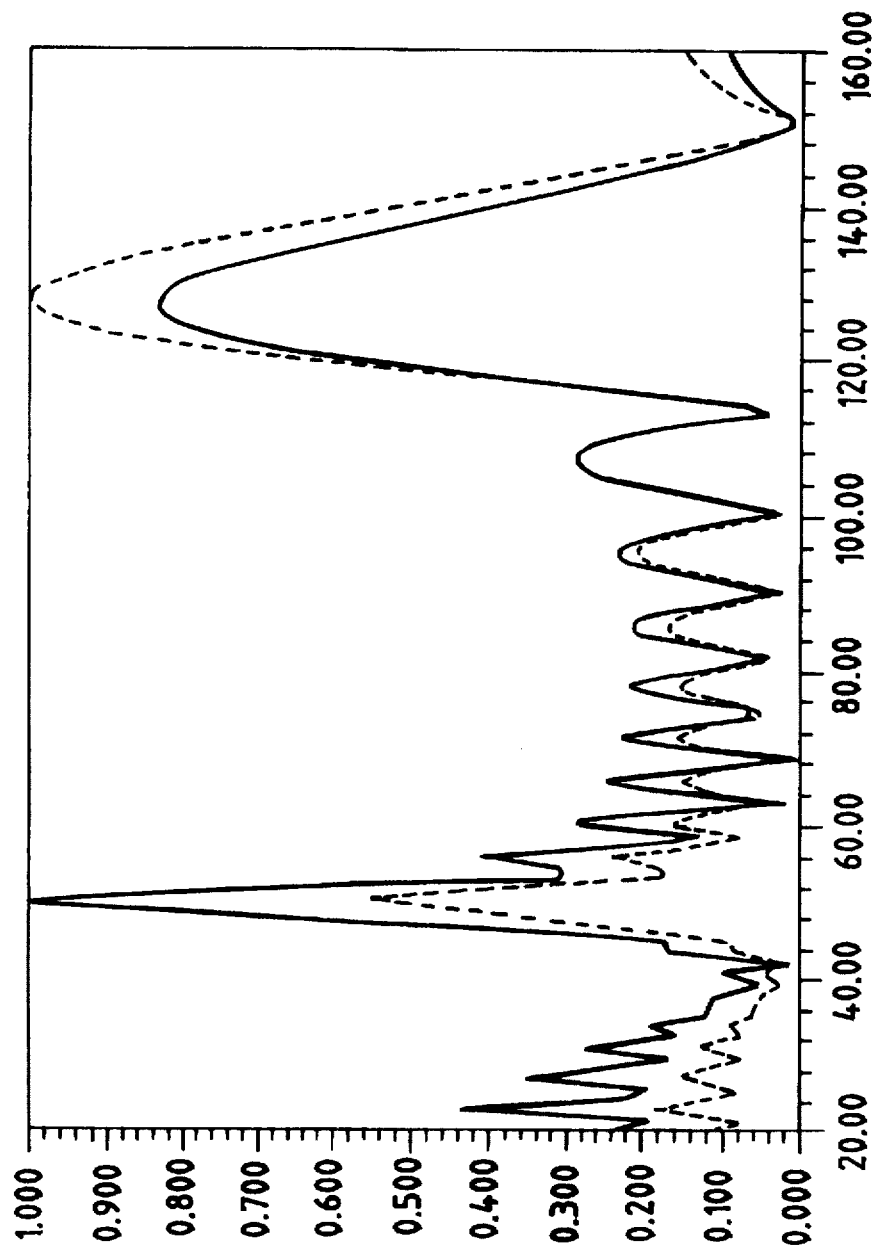
FIG. 4 is a curve similar to FIG. 3, however the focal point is 130 mm away from the transducer.

However, delays are used to focus at 130 mm, the curves of FIG. 4 are obtained where a secondary focusing appears around 50 mm. In fact, if one takes into account the absorption of tissues (see black curve), the pressure at the secondary focusing (50 mm) is higher than at the primary focusing (130 mm). Therefore, it is impossible to produce therapeutic treatments at 130 mm.

The discussion above shows that it is impossible to obtain a large variation in focal length when using sine wave electronic signals of the known type. The practical range of electronic focusing is very limited which makes the whole concept useless in a practical device. In addition it would even be sometimes impossible to treat a tissue at 130 mm as shown on FIG. 4.

Figure 5:
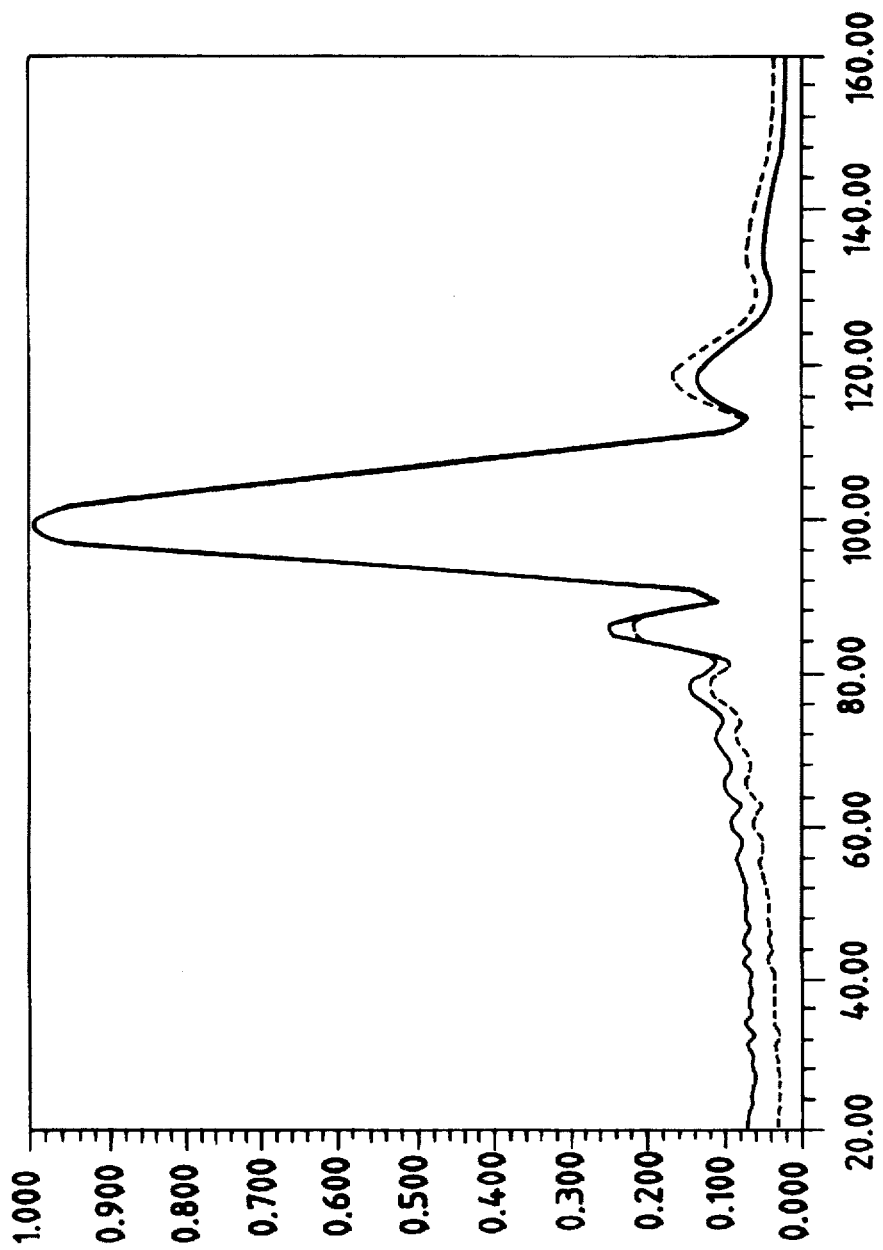
FIG. 5 represents a curve similar to FIG. 2 but now obtained with a sequence "M" pseudo random signal according to the present invention. There is no time delay between the transducers so that the focal point is at its geometric locus, i.e. 100 mm from the surface.
Figure 6:
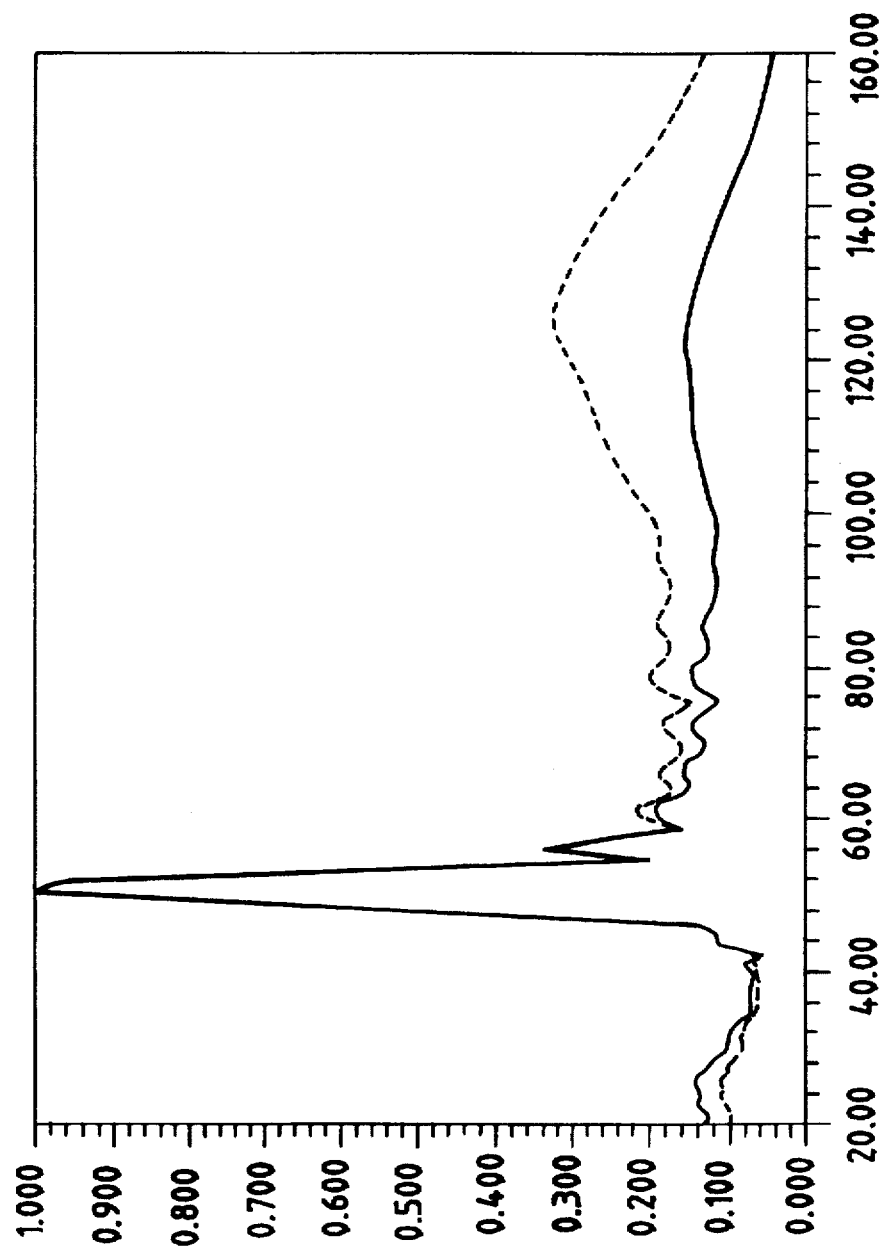
FIG. 6 represents a curve similar to FIG. 5 with the same "M" sequence pseudo random signal but with time delays between the rings so that the electronic focusing is 50 mm from the surface.
Figure 7:
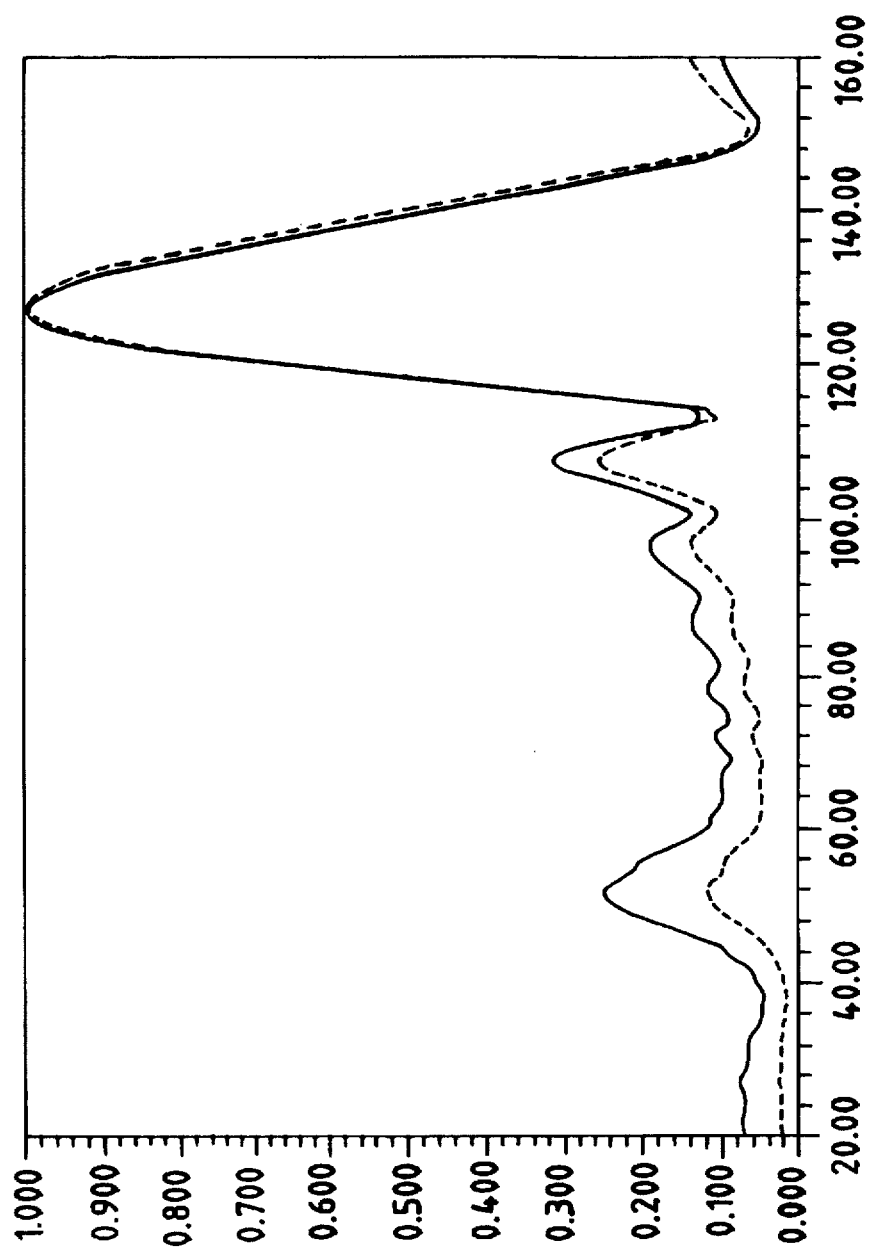
FIG. 7 represents a curve similar to FIGS. 5 and 6 with the same type of signals but with time delays between the rings such that the focusing is 130 mm from the surface.
Figure 8:
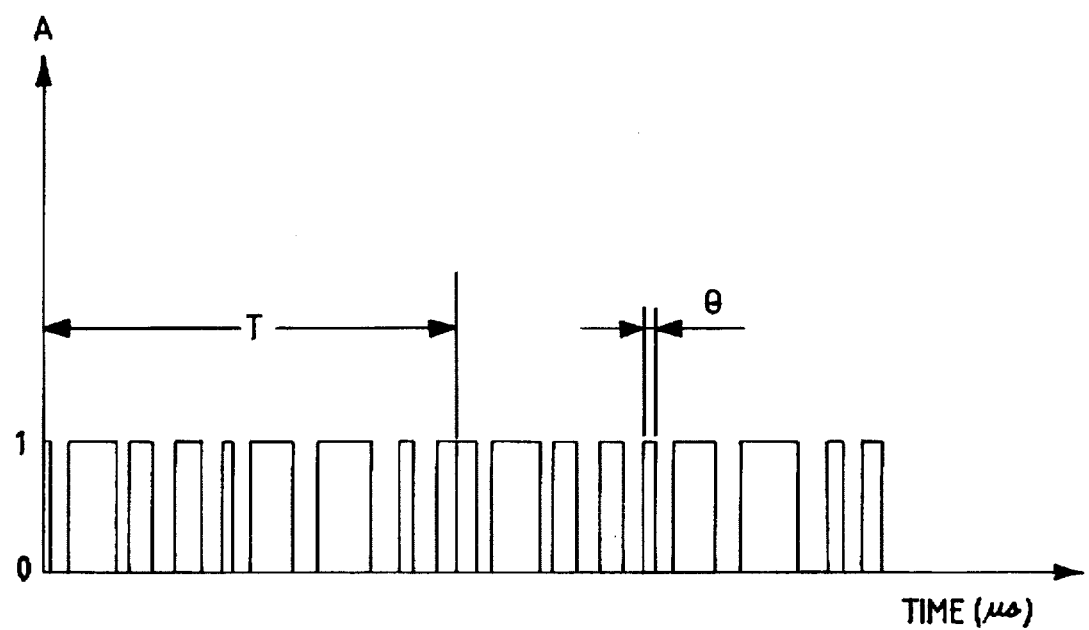
FIG. 8 represents a sequence "M" pseudo random binary coded signal which are more precisely described above, in which the amplitude is normalized to 1 and the time is in microseconds.

Referring now to FIGS. 5–7, which are produced with the process and the apparatus according to the invention, the major benefit of the invention is shown. The curves are produced using a sequence "M" Dirac-type autocorrelation function electronic signals such as the ones shown in FIG. 8.

When comparing FIG. 5 to FIG. 2, it is seen that Dirac-type autocorrelation function signal give the same good results as sine type signal when the focusing occurs at the geometrical focus F1 (here 100 mm from the surface). Therefore, the results are similar whether using the Dirac-type autocorrelation function signals or the sine signals. This confirms that the former can be used in a therapeutic application.

When one seeks to move the focal point well away from F1 by programming time delays as explained above, it is observed that a single focal zone is obtained (FIG. 6) whereas two focal zones are present with sine wave according to the prior art (FIG. 3). In both figures the time delays are according to the table above.

The same phenomenon can be observed when comparing curve in FIG. 7 (using pseudo random codes according to the invention) to FIG. 4 (using sine waves according prior art), i.e. the invention makes possible a single focusing zone.

Therefore, the invention makes possible therapeutic treatments of living tissues in a very reliable way. The treatment is efficient in a wide-range of focal distances when this was nearly impossible with the sine waves signals according to the prior art because the latter would produce secondary focal zones outside of the main focal zone.

It should be observed that all the elements of the embodiment described with reference to the figures form an integral portion of the invention and thus of the present description. The invention also covers any characteristic that appears to be novel over any of the prior art.

What is claimed is:

1. A method of electronically focussing a transducer having a plurality of piezoelectric elements, for treating living tissue, the method comprising the steps of: placing the living tissue in a position to be treated by the transducer; generating an electronic signal by a signal generator, said electronic signal having a Dirac-type autocorrelation function;

supplying the electronic signal to the plurality of piezoelectric elements such that the electronic signal supplied to each piezoelectric element is a delayed electronic signal delayed in time by a predetermined amount relative to the electronic signals supplied to the other piezoelectric elements and;

activating the piezoelectric elements with the delayed electronic signals such that the delayed electronic signals cause a secondary focusing of the transducer to be eliminated or minimized relative to a primary focusing of the transducer.

2. The method of claim 1, wherein the signal generator generates an electronic signal having a Dirac-type autocorrelation function which is used to modulate in phase a signal having a carrier frequency about equal to a nominal frequency of the transducer.

3. The method of claim 1, wherein the signal generator generates an electronic signal having a Dirac-type autocorrelation function which is used to modulate in frequency a signal having a carrier frequency about equal to a nominal frequency of the transducer.

4. The method of claim 1 wherein the signal generator generates a binary electronic signal having a Dirac-type autocorrelation function.

5. The method of claim 1 wherein the signal generator generates a random electronic signal of Gaussian or Poissonian type.

6. The method of claim 1 wherein the signal generator generates an electronic signal modulated in phase or in frequency.

7. The method of claim 1 wherein the signal generator generates a pseudo-random electronic signal coded with Golay codes.

8. The method of claim 1 wherein the signal generator generates a pseudo-random electronic signal coded with Barker codes.

9. The method of claim 1 wherein the signal generator generates a pseudo-random coded signal with a type M sequence having an elementary impulse duration τ about between about 0.1 μs and 100 μs, ideally of about 2 to 10 times an oscillating period of the transducer and having a repetition period T between about 1.0 μs and 10 seconds.

10. A therapeutic apparatus for treating living tissue comprising:

an ultrasonic transducer having a plurality of ultrasonic transducer elements;

a signal generator operatively coupled to the plurality of transducer elements to deliver electronic signals to the transducer elements, said electronic signals having a Dirac-type autocorrelation function;

a plurality of time delay circuits, each said time delay circuit operatively coupled between the signal generator and each transducer element such that the electronic signal delivered to each transducer element is delayed in time by a predetermined amount to reduce or minimize a secondary focusing of the transducer relative to a primary focusing of the transducer; and a controller operatively coupled to the signal generator and to the time delay circuits to provide the predetermined amount of time delay.

11. The apparatus of claim 10 wherein the controller directs the signal generator to deliver to the time delay circuits a random signal of type Gaussian or Poissonian.

12. The apparatus of claim 10 wherein the controller directs the signal generator to deliver to the time delay circuits a signal modulated in phase or in frequency.

13. The apparatus of claim 10 wherein the signal generator generates a pseudo-random coded signal with a type M sequence having an elementary impulse duration τ between about 0.1 μs and 100 μs, ideally of about 2 to 10 times the oscillating period of the transducer and having a repetition period T between about 1.0 μs and 10 seconds.

14. The apparatus of claim 10 wherein the signal generator delivers a pseudo-random coded signal with Golay or Barker codes.

15. The apparatus of claim 10 wherein said ultrasonic transducer has the shape of a spherical cup, the spherical cup being subdivided in the form of an annular array or a twodimensional array of piezoelectric elements, each said element being operatively coupled to an amplifier, each said amplifier being operatively coupled to each said time delay circuit such that the controller programs the time delay circuits with time delay values such that ultrasounds generated by each piezoelectric element form an ultrasonic beam focused on a common predetermined location in space relative to the spherical cup.

16. The apparatus of claim 15 wherein the transducer elements generate a therapeutic ultrasonic beam at a focal point relative to the spherical cup, said focal point being disposed within the living tissue to treat cancer lesions within the living tissue, said cancer lesions selected from the group of cancers consisting of prostate cancer, breast cancer, brain cancer and thyroid cancer.

* * * * *